United States Patent [19]
Kitagawara et al.

[11] Patent Number: 5,444,246
[45] Date of Patent: Aug. 22, 1995

[54] DETERMINING CARBON CONCENTRATION IN SILICON SINGLE CRYSTAL BY FT-IR

[75] Inventors: Yutaka Kitagawara; Hiroshi Kubota; Masaro Tamatsuka, all of Annaka, Japan

[73] Assignee: Shin-Etsu Handotai Co., Ltd., Tokyo, Japan

[21] Appl. No.: 127,522

[22] Filed: Sep. 28, 1993

[30] Foreign Application Priority Data

Sep. 30, 1992 [JP] Japan ................................ 4-285113

[51] Int. Cl.$^6$ ............................................ G01N 21/35
[52] U.S. Cl. ............................ 250/339.08; 250/341.4
[58] Field of Search ................ 250/339.08, 341, 358.1, 250/338.4, 341.4

[56] References Cited

U.S. PATENT DOCUMENTS

| | | | |
|---|---|---|---|
| 4,590,574 | 5/1986 | Edmonds et al. | 250/339.08 |
| 4,862,000 | 8/1989 | Kubota et al. | 250/341 |

FOREIGN PATENT DOCUMENTS

| | | |
|---|---|---|
| 0250707 | 1/1988 | European Pat. Off. . |
| 0473130A2 | 3/1992 | European Pat. Off. . |
| 58-135939 | 8/1983 | Japan .................... 250/341 |
| 61-22896 | 6/1986 | Japan .................... 250/341 |

OTHER PUBLICATIONS

American National Standard, "Standard Test Method for Substitutional Atomic Carbon Content of Silicon by Infrared Absorption", pp. 523–524, F123–70T, 1976.
G. K. Agopian et al., "Determination of Interstitial Oxygen in Silicon Using Internal Calibration with Two Phonon Peaks", IBM Technical Disclosure Bulletin, vol. 23, No. 4, Sep. 1980, pp. 1389–1390.
P. Stallhofer et al., "Oxygen and Carbon Measurements on Silicon Slices by the IR Method", *Solid State Technology*, vol. 26, No. 8, Aug. 1983, pp. 233–237.

*Primary Examiner*—Constantine Hannaher
*Assistant Examiner*—Edward J. Glick
*Attorney, Agent, or Firm*—Oliff & Berridge

[57] ABSTRACT

The substitutional carbon concentration in a silicon single crystal is determined by determining by FT-IR the infrared absorbance spectrum using as a reference a substantially carbon-free silicon single crystal having substantially the same degree of free carrier absorption and produced by the same process as the sample. A subtraction factor used in the determination is calculated from the infrared absorbance spectra of the sample and the reference. A subtraction spectrum indicating the difference between the sample and the reference at the relevant wave number for carbon is computed, and the carbon concentration in the sample is determined from the distance of the absorption peak of the subtraction spectrum of the localized vibration of substitutional carbon in the sample from a base line of the subtraction spectrum. An FT-IR carbon concentration determination apparatus embodying the method is also disclosed.

26 Claims, 13 Drawing Sheets

DETERMINATION OF CARBON CONCENTRATION IN SAMPLE OF LOW CARBON CONCENTRATION USING FZ-METHOD PRODUCED REFERENCE

DETERMINATION OF CARBON CONCENTRATION IN SAMPLE OF LOW CARBON CONCENTRATION USING FZ-METHOD PRODUCED REFERENCE

DETERMINATION OF CARBON CONCENTRATION

INFRARED ABSORBANCE SPECTRUM OF FZ-METHOD PRODUCED SILICON SINGLE CRYSTAL

SUBTRACTION SPECTRUM

DETERMINING CARBON CONCENTRATION IN SILICON SINGLE CRYSTAL BY FT-IR

BACKGROUND OF THE INVENTION

1. Field of the Invention

The present invention relates to determining the carbon concentration in a silicon single crystal by the Fourier transform infrared spectroscopy (FT-IR). It relates more particularly to a method and an apparatus of determining the substitutional carbon concentration in a silicon single crystal by the FT-IR using a reference of a silicon single crystal.

2. Description of the Related Art

Carbon and oxygen in a silicon single crystal wafer are important factors determining the quality of the wafer. FT-IR is widely employed for determining the carbon concentration in the wafer.

FIG. 9 illustrates an FT-IR optical system. The system comprises a source 1 of infrared light, an aperture device 2, a collimator 3 in the form of concave mirror, a Mickelson interferometer 4, a concave or converging mirror 8, an aperture device 10 and a sensor 11.

The aperture device 2 allows a divergent light from the source 1 of infrared light to pass. The collimator 3 receives the divergent light passing through the aperture device 2 and reflects a beam of collimated infrared light to the Mickelson interferometer 4.

The Mickelson interferometer 4 comprises a beam splitter 5, a fixed mirror 6 and a movable mirror 7. The beam splitter 5 receives the collimated beam from the collimator 3 and splits it into a beam of reflected infrared light and a beam of transmitted infrared light. The fixed mirror 6 reflects the beam of reflected infrared light from the beam splitter 5 back to the beam splitter 5. The movable mirror 7 reflects the beam of transmitted infrared light from the beam splitter 5 back to the beam splitter 5. The beam of reflected infrared light from the fixed mirror 6 and the beam of reflected infrared light from the movable mirror 7 meet at the beam splitter 5 and interfere with each other.

The converging mirror 8 receives the two interfering beams from the Mickelson interferometer 4 and transmits it to a sample 9 to be determined. The sensor 11 receives a light transmitting through the sample 9 and the aperture device 10. An analog/digital convertor (not shown) converts an interferogram output by the sensor 11 into a digital form which is then Fourier-transformed. Thus, an FT-IR concentration determination apparatus detects the infrared absorbance spectrum of the sample 9 and also the infrared absorbance spectrum of a reference in the same manner. FIG. 10 shows the infrared absorbance spectrum of a sample (p-type, 10 Ωcm) of a silicon single crystal produced by the Czochralski method (referred to as CZ-method produced silicon single crystal hereinafter). FIG. 11 shows the infrared absorbance spectrum of a reference (p-type, 2000 Ωcm) of a silicon single crystal produced by the floating zone method (referred to as FZ-method produced silicon single crystal hereinafter).

Usually, the FT-IR concentration determination apparatus previously detects the infrared absorbance spectrum of the reference and stores data thereof.

After producing the data of the infrared absorbance spectra of both the sample and the reference regarding the substitutional carbon Cs in a silicon crystal wafer, the FT-IR concentration determination apparatus computes a subtraction factor f for computing a subtraction spectrum between the infrared absorbance spectra of the sample and the reference. Subtracting a product of the subtraction factor and the infrared absorbance spectrum of the reference from the infrared absorbance spectrum of the sample provides the subtraction spectrum between the infrared absorbance spectra of the sample and the reference. FIG. 12 shows the subtraction spectrum between the infrared absorbance spectra of the sample and the reference of FIGS. 10 and 11.

Then, the FT-IR concentration determination apparatus determines the substitutional carbon concentration in the silicon single crystal wafer from the distance (i.e. the height) of the absorption peak of the localized vibration of the substitutional carbon appearing at 605 $cm^{-1}$ from a base line, for example, between 595 $cm^{-1}$ and 615 $cm^{-1}$. A determination of the substitutional carbon concentration provides 0.5 ppma from subtraction spectra of FIG. 12. The lower detective limit of the substitutional carbon concentration is on the order of 0.05 ppma according to the ASTM designation: F123-81.

The process for producing a silicon single crystal substrate for semiconductor devices is categorized into the Czochralski method and the floating zone method. The Czochralski method comprises the steps of placing a raw polysilicon in a quartz crucible, melting the raw polysilicon by a carbon heater, immersing a seed crystal of silicon single crystal in the surface of the melt, and lifting the seed crystal while rotating it to grow a silicon single crystal. The floating zone method comprises the steps of melting part of a raw polysilicon rod by a melting coil to produce a melting zone and moving the melting zone to grow a silicon single crystal.

In comparison, the CZ-method produced silicon single crystal contains more amounts of carbon and oxygen than the FZ-method produced silicon single crystal. It is assumed that carbon invades the CZ-method produced silicon single crystal from the carbon heater, etc. and oxygen invades the CZ-method produced silicon single crystal from the crucible. On the other hand, the FZ-method produced silicon single crystal is substantially carbon-free and oxygen-free. Thus, it has been considered that the FZ-method produced silicon single crystal is more appropriate to the reference for determining the carbon concentration and the oxygen concentration in the CZ-method produced silicon single crystal.

However, the present inventors researched and discovered that an employment of the FZ-method produced silicon single crystal as the reference had problems described below.

As shown in FIG. 13, the absorption peaks of the localized vibration of the substitutional carbon in silicon single crystals appear at 605 $cm^{-1}$ and overlap the intense absorption peaks of the silicon phonon. In addition, the forms of the absorption peaks of silicon phonon depend on degrees of free carrier absorption of a dopant and are difference when silicon single crystal wafers have resistivities of 3 Ωcm and 20 Ωcm.

Thus, the other effects on differences absorbance between the sample and the reference except the localized vibration peaks of the substitutional carbon and, particularly, the effect of the absorption by the intense silicon phonon and free carriers must be as reduced as possible so that the FT-IR concentration determination apparatus can exactly extract the absorption peak of the localized vibration of the substitutional carbon as the substraction spectrum between the sample and the reference. Therefore, a reference having essentially the same degree of absorption by the silicon phonon and essentially the same degree of free carrier absorption of a dopant which overlap the absorption peak of the localized vibration of the substitutional carbon as a sample must be employed.

However, since the resistivity of the sample of the CZ-method produced silicon single crystal is 20 Ωcm or less in almost all cases and the resistivity of the reference of the FZ-method produced silicon single crystal, which is normally produced without a dopant, is 1000 Ωcm or more, the degrees of free carrier absorption of the dopant in the sample and in the reference differ by a large amount.

In addition, the dopant concentration and the oxygen concentration in the FZ-methodical silicon single crystal are much smaller than those in the CZ-method produced silicon single crystal. Thus, the degrees of free carrier absorption of the dopant and the forms of the absorption peak curves by the silicon phonon of the sample and the reference differ greatly from each other. Thus, the absorption peak of the localized vibration of the substitutional carbon is deformed and it is difficult to precisely determine the substitutional carbon concentration of 0.1 ppma or less.

In addition, conventional methods of determining the subtraction factor have a problem in improving the precision. That is, a conventional FT-IR carbon concentration determination apparatus computes the subtraction factor f as a simple ratio of the infrared absorbance ($As(\kappa)$) of a sample to the infrared absorbance ($Ar(\kappa)$) of a reference at a specified wave number $\kappa$ by the following equation (1):

$$As(\kappa) - f \times Ar(\kappa) = 0 \quad (1),$$

or as a ratio of an integral of the infrared absorbance ($As(\kappa)$) of a sample to an integral of the infrared absorbance ($Ar(\kappa)$) of a reference between the limits $\kappa = \kappa l$ and $\kappa = \kappa h$ in terms of wave number by the following equation (2):

$$\int_{\kappa=\kappa l}^{\kappa=\kappa h} As(\kappa)d\kappa - f \times \int_{\kappa=\kappa l}^{\kappa=\kappa h} Ar(\kappa)d\kappa = 0. \quad (2)$$

Since wave number $\kappa$ is actually determined by a certain resolution, wave numbers are not analog values but discreet values $\kappa n$ ($n=1, 2, 3 \ldots$). Thus, the equation (2) is actually transformed into the equation (3):

$$\sum_{\kappa=l}^{\kappa=h} As(\kappa) - f \times \sum_{\kappa=l}^{\kappa=h} Ar(\kappa) = 0. \quad (3)$$

When computing the subtraction factor by the equation (1), (2) or (3) and the subtraction spectrum using the subtraction factor, the conventional FT-IR carbon concentration determination apparatus cannot suppress aging and the effects of state differences between the sample and the reference (e.g. differences in the thickness and the resistivity) to be least enough so as to be free from the effects of the state differences. Thus, the repeatability of the determination of the same apparatus is poor and errors in the determination between any two conventional FT-IR carbon concentration determination apparatuses of different types are intolerably high.

In wafers of silicon single crystal of today, a required level of the carbon concentration has come down to under 0.05 ppma and the resolution power of the FT-IR carbon concentration determination apparatus has been impressive because of a high quality substrate in use for highly integrated devices and a high-purity device manufacturing process.

SUMMARY OF THE INVENTION

In view of the situation described above, a primary object of the present invention is to provide a method and an apparatus of precisely determining a carbon concentration in silicon single crystals.

In order to achieve this object, a first aspect of the present invention in a method of determining the substitutional carbon concentration in a silicon single crystal by FT-IR comprises the steps of determining by FT-IR the infrared absorbance spectrum of a sample of a silicon single crystal the substitutional carbon concentration of which is to be determined, determining by FT-IR the infrared absorbance spectrum of a reference of a substantially carbon-free silicon single crystal of substantially the same degree of free carrier absorption as the sample, the reference being produced by the same process as the sample, computing a subtraction factor from the infrared absorbance spectra of the sample and the reference by the equation (1), (2) or (3):

$$As(\kappa) - f \times Ar(\kappa) = 0, \quad (1)$$

$$\int_{\kappa=\kappa l}^{\kappa=\kappa h} As(\kappa)d\kappa - f \times \int_{\kappa=\kappa l}^{\kappa=\kappa h} Ar(\kappa)d\kappa = 0, \quad (2)$$

$$\sum_{\kappa=l}^{\kappa=h} As(\kappa) - f \times \sum_{\kappa=h}^{\kappa=l} Ar(\kappa) = 0, \quad (3)$$

computing a subtraction spectrum between the infrared absorbance spectra of the sample and the reference using the computed subtraction factor and determining the substitutional carbon concentration in the sample from a distance to the absorption peak of the subtraction spectrum of the localized vibration of a substitutional carbon in the sample from a base line of the subtraction spectrum.

A second aspect of the present invention in an apparatus of determining a substitutional carbon density in a silicon single crystal by FT-IR comprises means for determining by FT-IR the infrared absorbance spectrum of a sample of a silicon single crystal the substitutional carbon concentration of which is to be determined, means for storing data of the infrared absorbance spectra determined by FT-IR of multiple references of substantially carbon-free silicon single crystals of different degrees of free carrier absorption, means for selecting from the data of the infrared absorbance spectra of the references in said storage means data of the infrared absorbance spectrum of a reference of substantially the same degree of free carrier absorption as the sample, means for computing from the infrared absorbance spectra of the reference and the sample a subtraction factor by the equation (1), (2) or (3), or by a least square approximation so that within lower and higher ranges of wave number than the absorption peak of the subtraction spectrum of the localized vibration of the substitutional carbon a relational expression between wave number and infrared absorbance is approximate to an equation, means for computing a subtraction spectrum between the infrared absorbance spectra of the sample and the reference using the computed subtraction factor, and determining the substitutional carbon density in the sample from the computed subtraction spectrum.

The apparatus of the second aspect of the present invention may further comprise means for determining by FT-IR the infrared absorbance spectra of the references. The apparatus of the second aspect of the present invention may be automated.

Another object of the present invention is to provide a method and an apparatus of precisely determining a substitutional carbon concentration in a CZ-method produced silicon single crystal.

In order to achieve this object, a third aspect of the present invention in a method of determining a substitutional carbon density in a CZ-method produced silicon single crystal by FT-IR comprises the steps of determining by the FT-IR infrared absorbance spectrum of a sample of the CZ-method produced silicon single crystal the substitutional carbon density of which is to be determined, determining by FT-IR the infrared absorbance spectrum of a reference of a substantially carbon-free CZ-method produced silicon single crystal of substantially the same degree of free carrier absorption as the sample, computing a subtraction factor from the infrared absorbance spectra of the sample and the reference by the equation (1), (2) or (3), computing a subtraction spectrum between the infrared absorbance spectra of the sample and the reference using the computed subtraction factor, and determining the substitutional carbon concentration in the sample from a distance of the absorption peak of the subtraction spectrum of the localized vibration of a substitutional carbon in the sample from a base line of the subtraction spectrum.

Specifically, FIG. 2 shows an example of the subtraction spectrum computed by the method of the third aspect of the present invention. The method of the third aspect of the present invention employs a sample of a p-type CZ-method produced silicon single crystal of a resistivity of 10 $\Omega$cm and a carbon concentration of about 0.05 ppma as the sample of FIG. 1 and a reference of a substantially carbon-free p-type CZ-method produced silicon single crystal of a resistivity of 20 $\Omega$cm and computes the subtraction spectrum by the equation (1), (2) or (3). FIG. 2 shows the absorption peak of the localized vibration of the substitutional carbon.

On the other hand, FIG. 1 shows an example of the subtraction spectrum determined by a prior-art method of determining the carbon concentration. This method employs the same sample of the p-type CZ-method produced silicon single crystal of the resistivity of 10 $\Omega$cm and the carbon concentration of about 0.05 ppma and a reference of a p-type FZ-method produced silicon single crystal of the resistivity of 2000 $\Omega$cm and computes a subtraction spectrum by the equation (1), (2) or (3).

In the fourth aspect of the present invention, the subtraction factor computing step of the first and third aspects of the present invention comprises the step of computing the subtraction factor by a least square approximation so that within lower and higher ranges of wave number than the absorption peak of the subtraction spectrum of the localized vibration of the substitutional carbon a relational expression between wave number and infrared absorbance is approximate to a linear or quadratic equation.

As described above, subtracting a product of the subtraction factor $f$ and the infrared absorbance spectrum of the reference from the infrared absorbance spectrum of the sample provides the subtraction spectrum. Thus, the value of the subtraction factor directly changes the form of the subtraction spectrum.

FIG. 3 shows different forms of subtraction spectra when the subtraction factor has different values. In a case of FIG. 3, the p-type CZ-method produced silicon single crystal of the resistivity of 10 $\Omega$cm and a substitutional carbon concentration of about 0.05 ppma was employed as the sample and a substantially carbon-free p-type CZ-method produced silicon single crystal of the resistivity of 20 $\Omega$cm was employed as the reference. The subtraction factors $f$ were 0.975, 0.985, 0.995, 1.005, 1.015 and 1.025. In particular, a subtraction factor $f$ appropriate to the determination of the carbon concentration was 0.995 at which a part of a curve having a wave number higher than the absorption peak of the localized vibration of the substitutional carbon and a part of the curve having a wave number lower than the absorption peak of the localized vibration of the substitutional carbon are flattest.

However, since a commercially sold in-line FT-IR carbon concentration determination apparatus for determining the carbon concentrations of a large number of samples computes the difference subtraction factor by the equation (1), (2) or (3), it cannot provides the optimum subtraction factor (i.e. $f=0.995$). The determined value is relatively stable because the absorption peak of the localized vibration of the substitutional carbon is high, when the substitutional carbon concentration exceeds 0.1 ppma. On the other hand, when the substitutional carbon concentration in the sample is 0.1 ppma or lower, the in-line FT-IR carbon concentration determination apparatus has a large error in the determination of the carbon concentration. Therefore, the third aspect of the present invention provides the method of computing the optimum subtraction factor (i.e. $f=0.995$) by the equation (4):

$$S = \int_{\kappa=\kappa l1}^{\kappa=\kappa h1} [(As(\kappa) - f \times Ar(\kappa)) - (b\kappa + a)]^2 d\kappa + \int_{\kappa=\kappa l2}^{\kappa=\kappa h2} [(As(\kappa) - f \times Ar(\kappa)) - (b\kappa + a)]^2 d\kappa. \quad (4)$$

Thus, both the part of the curve of the subtraction spectrum having a wave number more than the absorption peak of the localized vibration of the substitutional carbon and the part of the curve of the subtraction spectrum having a wave number less than the absorption peak of the localized vibration of the substitutional carbon are substantially flat. Since wave number $\kappa$ is actually determined by a certain resolution, wave numbers are not analog values but discrete values $\kappa n$ ($n=1, 2, 3 \ldots$). Thus, the equation (4) is actually transformed into the equation (5):

$$S = \int_{\kappa=\kappa l1}^{\kappa=\kappa h1} [(As(\kappa) - f \times Ar(\kappa)) - (b\kappa + a)]^2 + \int_{\kappa=\kappa l2}^{\kappa=\kappa h2} [(As(\kappa) - f \times Ar(\kappa)) - (b\kappa + a)]^2. \quad (5)$$

Specifically, a range of wave number of $\kappa l1$ to $\kappa h1$ is selected as a range of larger wave numbers than the absorption peak of the localized vibration of the substitutional carbon and a range of wave number of $\kappa l2$ to $\kappa h2$ is selected as a range of less wave numbers than the absorption peak of the localized vibration of the substitutional carbon. The method of the fourth aspect of the present invention computes the subtraction factor by the equation (5) so that in the both ranges the subtraction spectrum is closely approximated with respect to wave number being represented in a linear equation. For example, the lower range of wave number covers 550–595 cm$^{-1}$ (i.e. $\kappa l1=550$, $\kappa h1=595$) and the higher range of wave number covers 615–660 cm$^{-1}$ ($\kappa l2=615$, $\kappa h2=660$).

In the case of FIG. 3, the reference of the same type conductivity and substantially the same resistivity as the sample was employed. When the resistivity of a sample is lower than that of the sample of FIG. 3, a base line of the subtraction spectrum is curved. In this case, the subtraction spectrum is approximated by the quadratic equation (6) instead of the linear equations (4) and (5) so that the equation (6) provides an optimum subtraction factor:

$$S = \int_{\kappa=\kappa l1}^{\kappa=\kappa h1} [(As(\kappa) - f \times Ar(\kappa)) - (c\kappa + b\kappa + a)]^2 d\kappa + \int_{\kappa=\kappa l2}^{\kappa=\kappa h2} [(As(\kappa) - f \times Ar(\kappa)) - (c\kappa + b\kappa + a)]^2 d\kappa. \quad (6)$$

Since wave number $\kappa$ is actually determined by a certain resolution, wave numbers are not analog values but discrete values $\kappa n$ ($n=1, 2, 3...$). Thus, the equation (6) is actually transformed into the equation (7):

$$S = \int_{\kappa=\kappa l1}^{\kappa=\kappa h1} [(As(\kappa) - f \times Ar(\kappa)) - (c\kappa^2 + b\kappa + a)]^2 d\kappa + \int_{\kappa=\kappa l2}^{\kappa=\kappa h2} [(As(\kappa) - f \times Ar(\kappa)) - (c\kappa^2 + b\kappa + a)]^2 d\kappa. \quad (7)$$

FIG. 4 shows subtraction spectra between the same sample and the same reference computed by the equations (1) and (2) as those of the case of FIG. 3. In FIG. 4, the curve in dashed line shows the subtraction spectrum computed by the equation (1) and the curve in solid line shows the subtraction spectrum computed by the equation (2). Neither the curve in dashed line nor the curve in solid line shows the absorption peak of the localized vibration of the substitutional carbon.

A fifth aspect of the present invention in an apparatus of determining the substitutional carbon concentration in a CZ-method produced silicon single crystal by FT-IR comprises means for determining by the FT-IR the infrared absorbance spectrum of sample of the CZ-method produced silicon single crystal the substitutional carbon concentration of which is to be determined, means for storing data of the infrared absorbance spectra determined by FT-IR of multiple references of the substantially carbon-free CZ-method produced silicon crystals of different degrees of free carrier absorption, means for selecting from the data of the infrared absorbance spectra of the references in said storage means data of the infrared absorbance spectrum of a reference of substantially the same degree of free carrier absorption as the sample, means for computing from the infrared absorbance spectra of the reference and the sample a subtraction factor by the equation (1), (2) or (3), or by a least square approximation so that within lower and higher ranges of wave number than the absorption peak of the subtraction spectrum of the localized vibration of the substitutional carbon a relational expression between wave number and infrared absorbance is approximate to an equation, means for computing a subtraction factor spectrum between the infrared absorbance spectra of the sample and the reference using the computed subtraction factor, and determining the substitutional carbon concentration in the sample from the computed subtraction spectrum by a predetermined relation between carbon concentration and subtraction spectrum.

The FT-IR carbon concentration determination apparatus of the fifth aspect of the present invention may be automated.

Since the third aspect of the present invention employs the reference of the carbon-free CZ-method produced silicon single crystal of substantially the same degree of free carrier absorption as the sample, the residues of the infrared absorbance spectra of the sample and the reference except the absorption peak of the localized vibration of the substitutional carbon can be substantially the same in extracting the absorption peak of the localized vibration of the substitutional carbon.

This will be described with reference to FIGS. 1 and 2. As seen in FIG. 2, the absorption peak (i.e. the hatched area) of the localized vibration of the substitutional carbon is distinct. On the other hand, the absorption peak of the localized vibration of the substitutional carbon, as seen in FIG. 1, is indistinct.

In order to achieve the distinct absorption peak of FIG. 2, the third aspect of the present invention employs the reference of the same CZ-method produced p-type silicon single crystal as the sample. This reference has substantially the same resistivity as the reference of the FZ-method produced silicon single crystal, so that this reference and the sample have substantially the same degree of free carrier absorption. In addition, since this reference is substantially carbon-free, the absorption peak of the localized vibration of the substitutional carbon in the sample is distinct. Thus, the employment of the reference of the substantially carbon-free CZ-method produced silicon single crystal of substantially the same degree of free carrier absorption as the sample provides the distinct absorption peak of the localized vibration of the substitutional carbon even when the sample has a carbon concentration of 0.1 ppma or lower.

The fourth aspect of the present invention can reduce the effects of differences in states (thickness and resistivity) between the sample and the reference even when the sample has the carbon concentration of 0.1 ppma or lower. The inventive method of computing the subtraction factor by the equation (5) can distinctively extract the absorption peak of the localized vibration of the substitutional carbon when the subtraction spectrum is determined using the same sample and reference as those of the case of FIG. 4. Thus, the fourth aspect of the present invention can precisely determine the substitutional carbon density in the sample.

On the other hand, the both curves, as seen in FIG. 4, indicate the effect of the absorption peak by silicon when a conventional computer software for the FT-IR carbon concentration determination computes the subtraction spectrum by the equation (1) or (2), so that this effect makes indistinct the absorption peak of the localized vibration of the substitutional carbon.

The second and fifth aspects of the present invention can select the infrared absorbance spectrum of an optimum reference from the infrared absorbance spectra of the references and compute the subtraction spectrum, so that even an in-line FT-IR carbon density determination apparatus embodying the fourth aspect of the present invention can precisely determine the carbon concentration in the CZ-method produced silicon single crystal.

The present invention can increase the determination repeatability of the same FT-IR carbon concentration determination apparatus and reduce a determination error between FT-IR carbon concentration determination apparatuses. Specifically, the determination repeatability was increased to triple and the determination error was reduced to ⅓ in a test conducted using FT-IR carbon concentration determination apparatuses of the inventors.

Other objects, features and advantages of the present invention will be apparent from a consideration of the following description, taken in connection with the accompanying drawings.

DESCRIPTION OF THE PREFERRED EMBODIMENT

Figure 1:
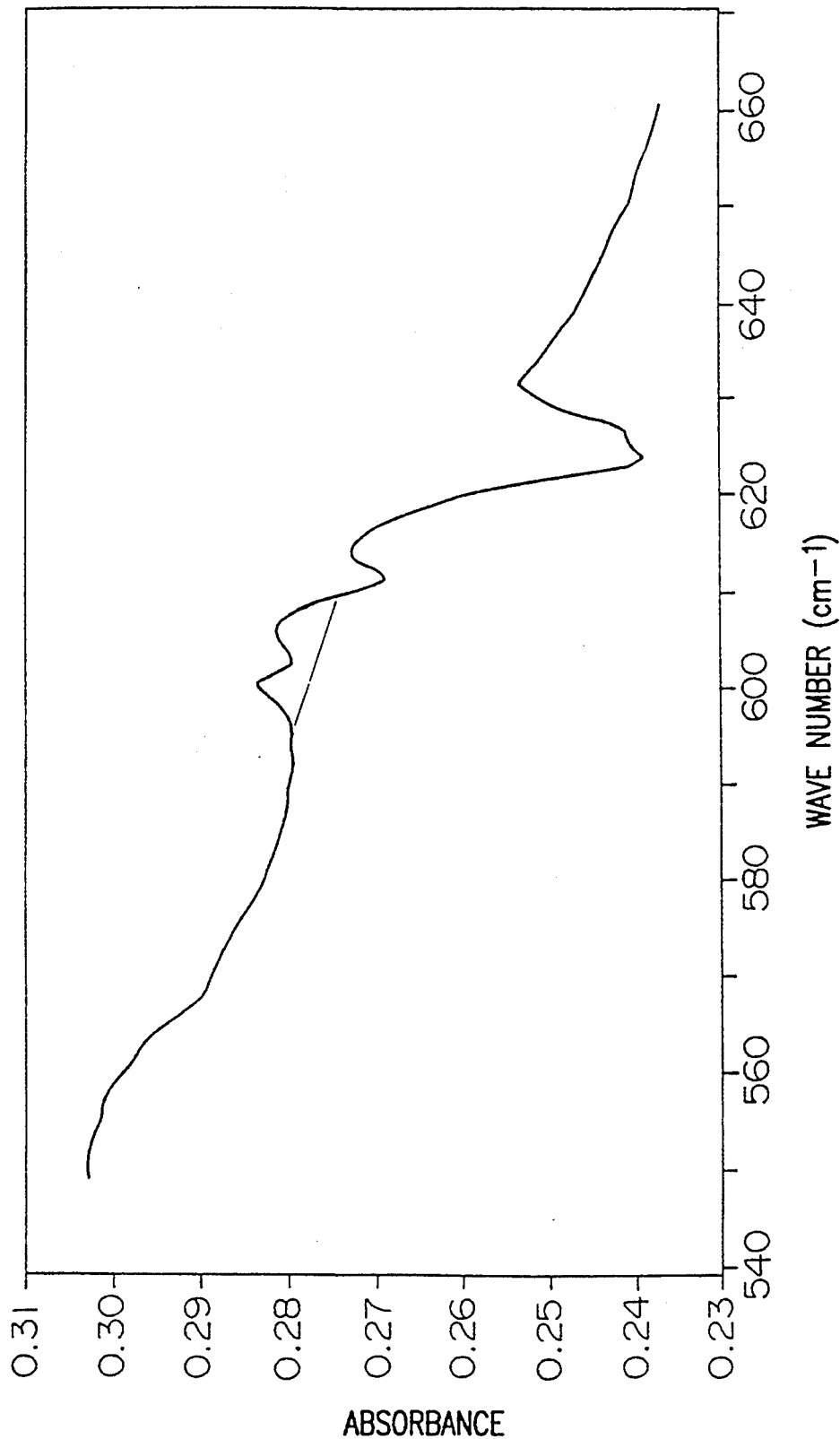
FIG. 1 is a graph of an infrared difference absorbance, determined by a prior-art method, between a sample of a CZ-method produced silicon single crystal and a reference of a FZ-method produced silicon single crystal.
Figure 2:
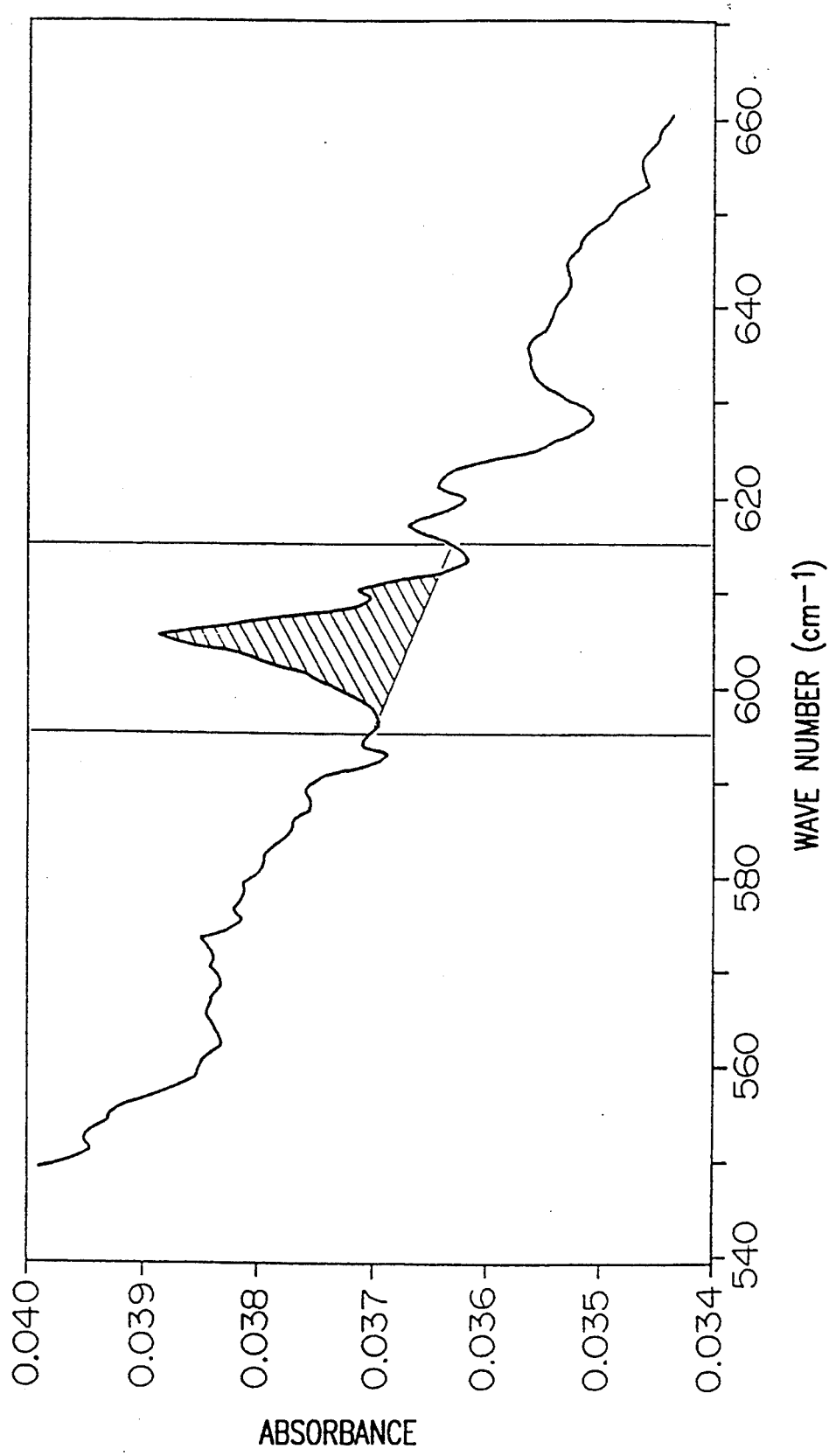
FIG. 2 is a graph of an infrared difference absorbance, determined by an inventive method, between a sample of a CZ-method produced silicon single crystal and a reference of a CZ-method produced silicon single crystal.
Figure 3:
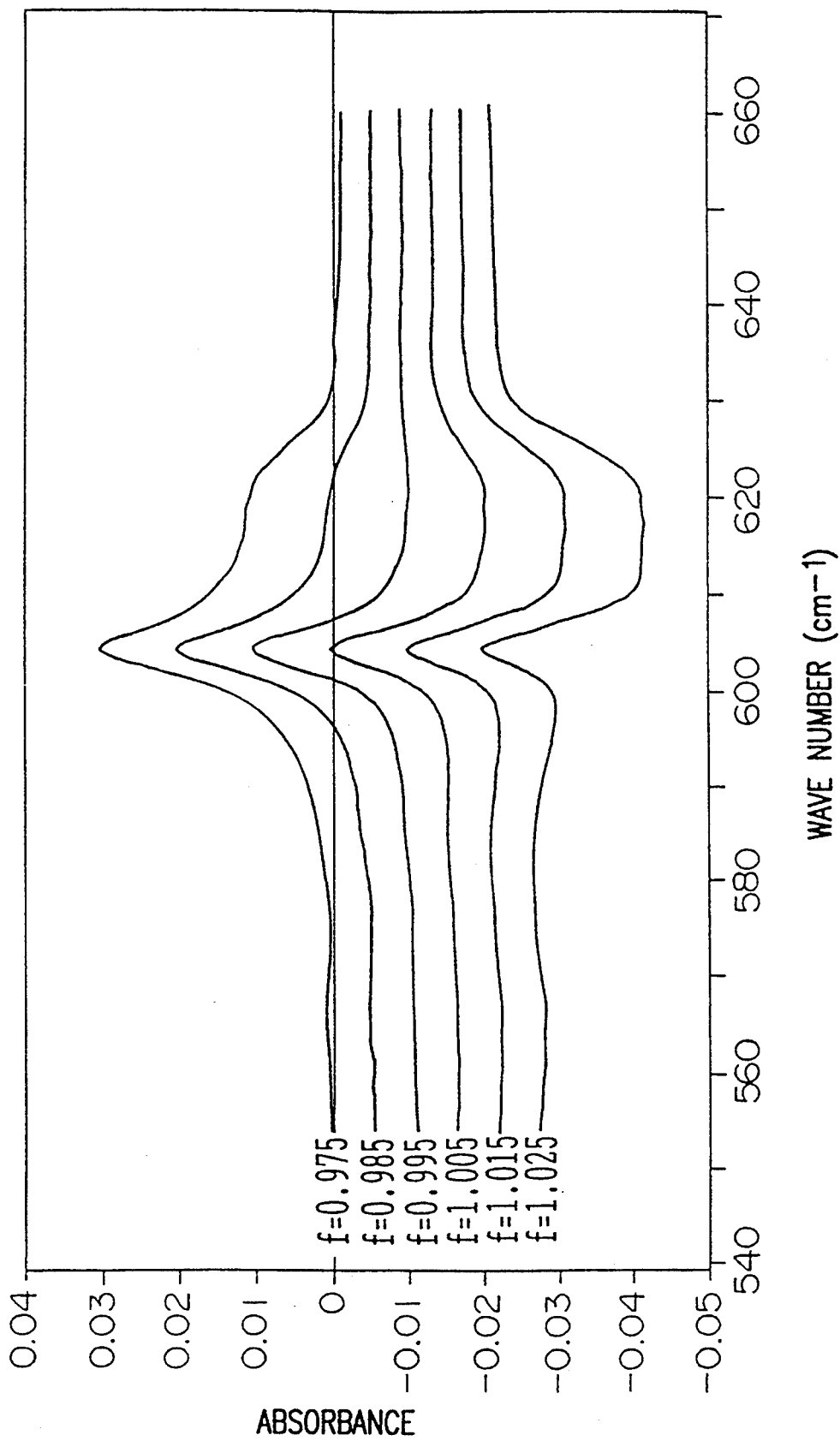
FIG. 3 is a graph of subtraction infrared spectra of different forms with different subtraction factors.
Figure 4:
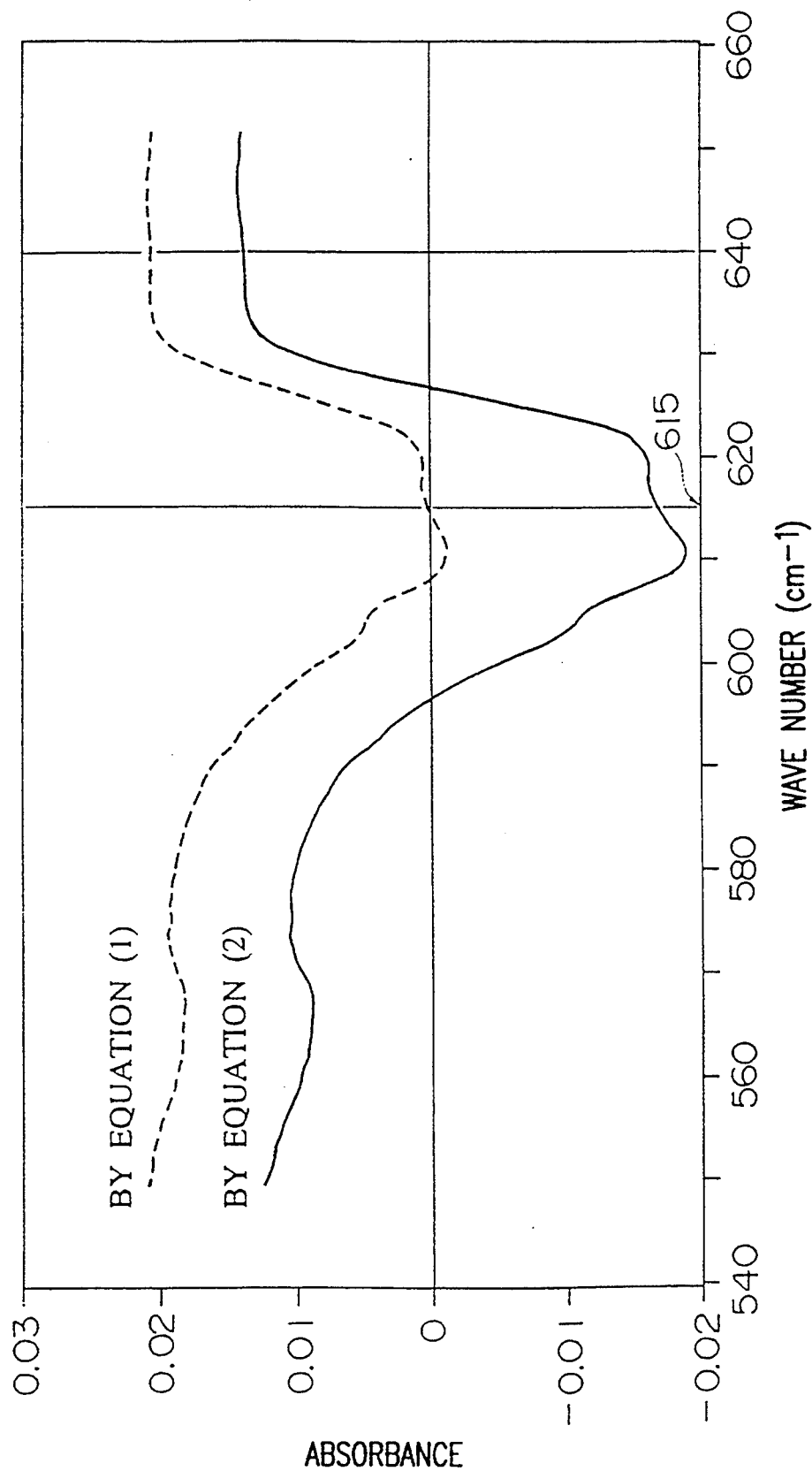
FIG. 4 is a graph of subtraction spectra when a conventional FT-IR carbon concentration determination computer software determines the carbon concentration in the CZ-method produced silicon single crystal.

A preferred embodiment of the present invention will be described with reference to the drawings hereinafter.

An FT-IR carbon concentration determination apparatus of the present invention comprises a storage for storing data of the infrared absorbance spectra of different references. The FT-IR carbon concentration determination apparatus determines the infrared absorbance spectra of samples by FT-IR, subtraction spectra from the infrared absorbance spectra of the determined samples and the stored references, and the substitutional carbon concentrations in the samples from the subtraction spectra.

When a wafer of a CZ-method (which is a main method of producing silicon single crystal) produced silicon single crystal is employed as a sample the carbon concentration of which is to be determined, the inventive FT-IR-carbon concentration determination apparatus and method employ a reference of a CZ-method produced silicon single crystal of a very low carbon concentration. Since a method of producing a silicon single crystal by the CZ-method comprises the steps of melting a raw polysilicon in a quartz crucible by a carbon heater, immersing a seed crystal in the surface of the melt and gradually lifting the seed crystal to produce a silicon single crystal, the CZ-method produced silicon crystal takes carbon derived from the raw polysilicon and the carbon heater. An amount of taken-in carbon increases towards the tail of a silicon single crystal rod by the segregation of the carbon. Thus, a silicon single crystal wafer sliced from a head (adjoining the seed crystal) of the silicon single crystal rod which is produced from a raw polysilicon of a minute carbon concentration provides a substantially carbon-free CZ-method produced reference. The storage of the FT-IR carbon concentration determination apparatus previously stores data of the infrared absorbance spectra of references of carbon-free CZ-method produced silicon single crystals of different degrees of free carrier absorption which are sliced as described above. Alternatively, the data of the infrared absorbance spectra of the references may be obtained by another method.

After the storage of the data, the FT-IR carbon concentration determination apparatus determines the infrared absorbance spectra of different samples, automatically select data of the infrared absorbance spectrum of a reference of substantially the same degree of free carrier absorption as a sample to be determined from the data of the infrared absorbance spectra of the references in the storage, and computes the subtraction spectrum between the infrared absorbance spectra of the sample and the reference. The FT-IR carbon concentration determination apparatus computes a subtraction factor f by a least square approximation so that within ranges of wave number lower and higher than the absorption peak of the localized vibration of the substitutional carbon a relational expression of wave number and absorbance of the difference absorbance spectrum is most approximate to a linear or quadratic equation, and the subtraction spectrum from the subtraction factor.

Figure 5:
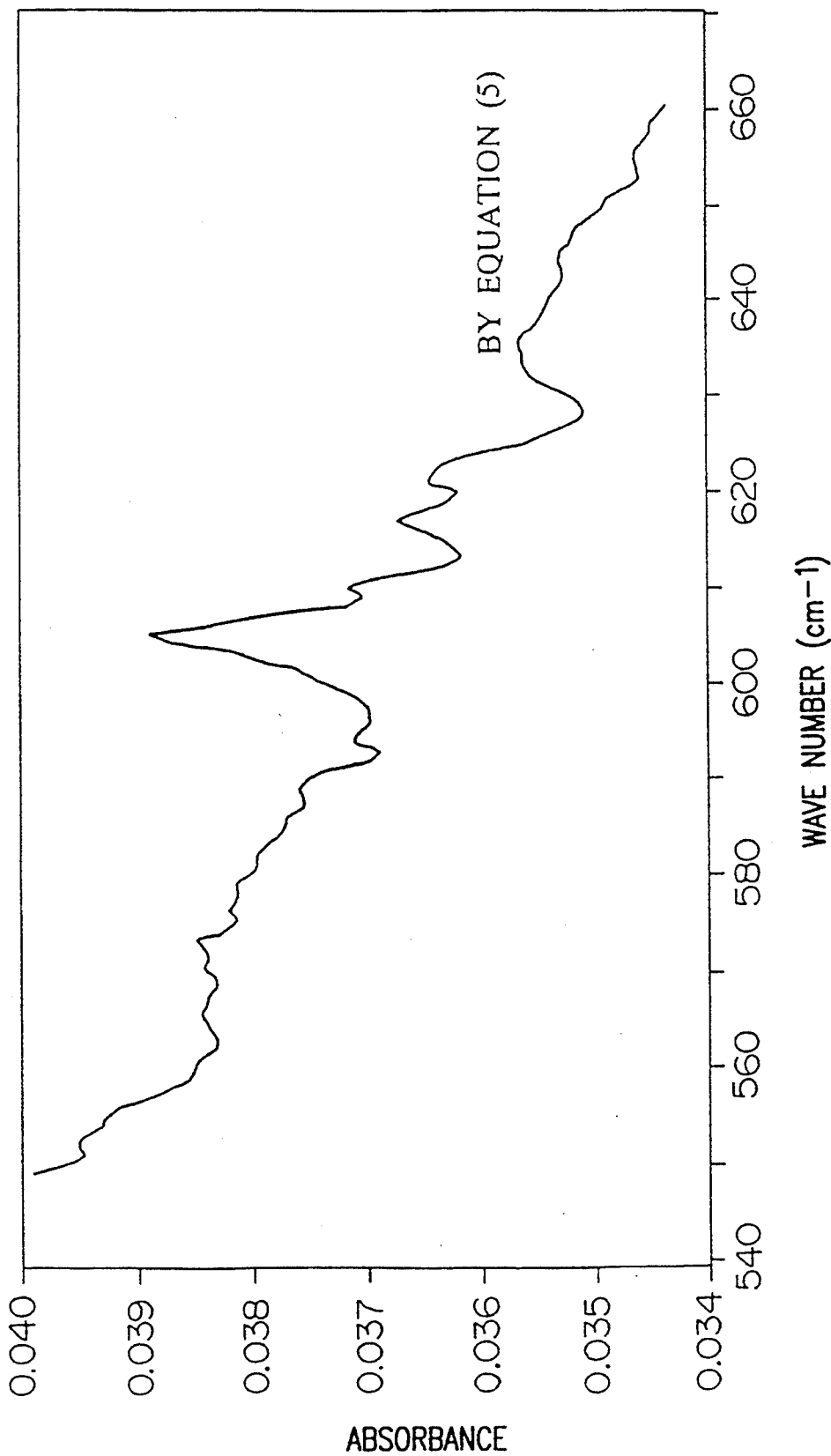
FIG. 5 is a graph of subtraction spectra when the inventive FT-IR carbon concentration determination method (e.g. a FT-IR carbon concentration determination computer software) determines the carbon concentration in the CZ-method produced silicon single crystal.

FIG. 5 is a graph of subtraction spectra using the FT-IR carbon concentration determination method with a CZ-method produced single crystal reference and sample and using a subtraction factor computed using equation (5).

Figure 6:
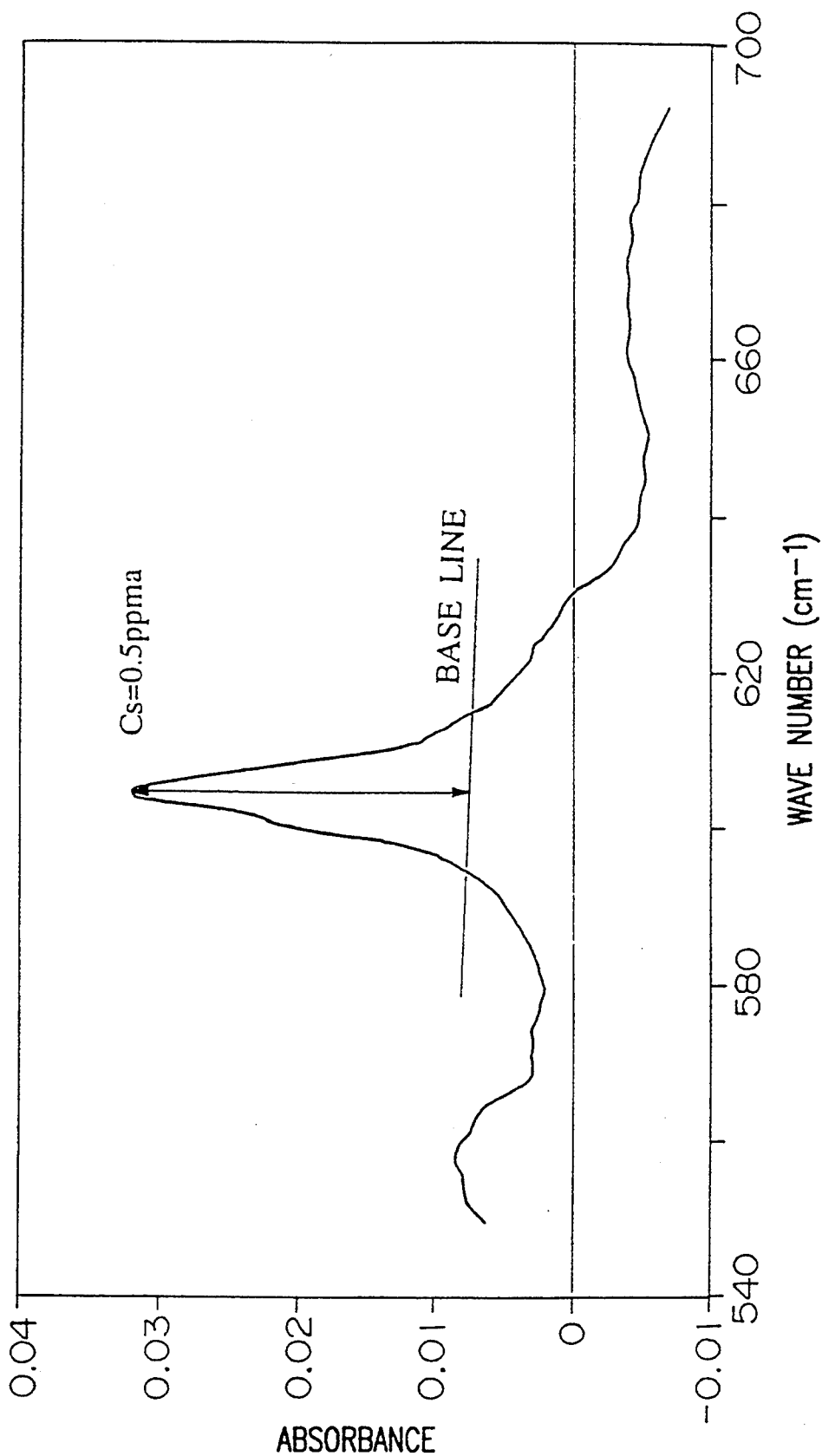
FIG. 6 is a graph indicative of the carbon concentration determination using the subtraction spectrum of FIG. 5.
Figure 7:
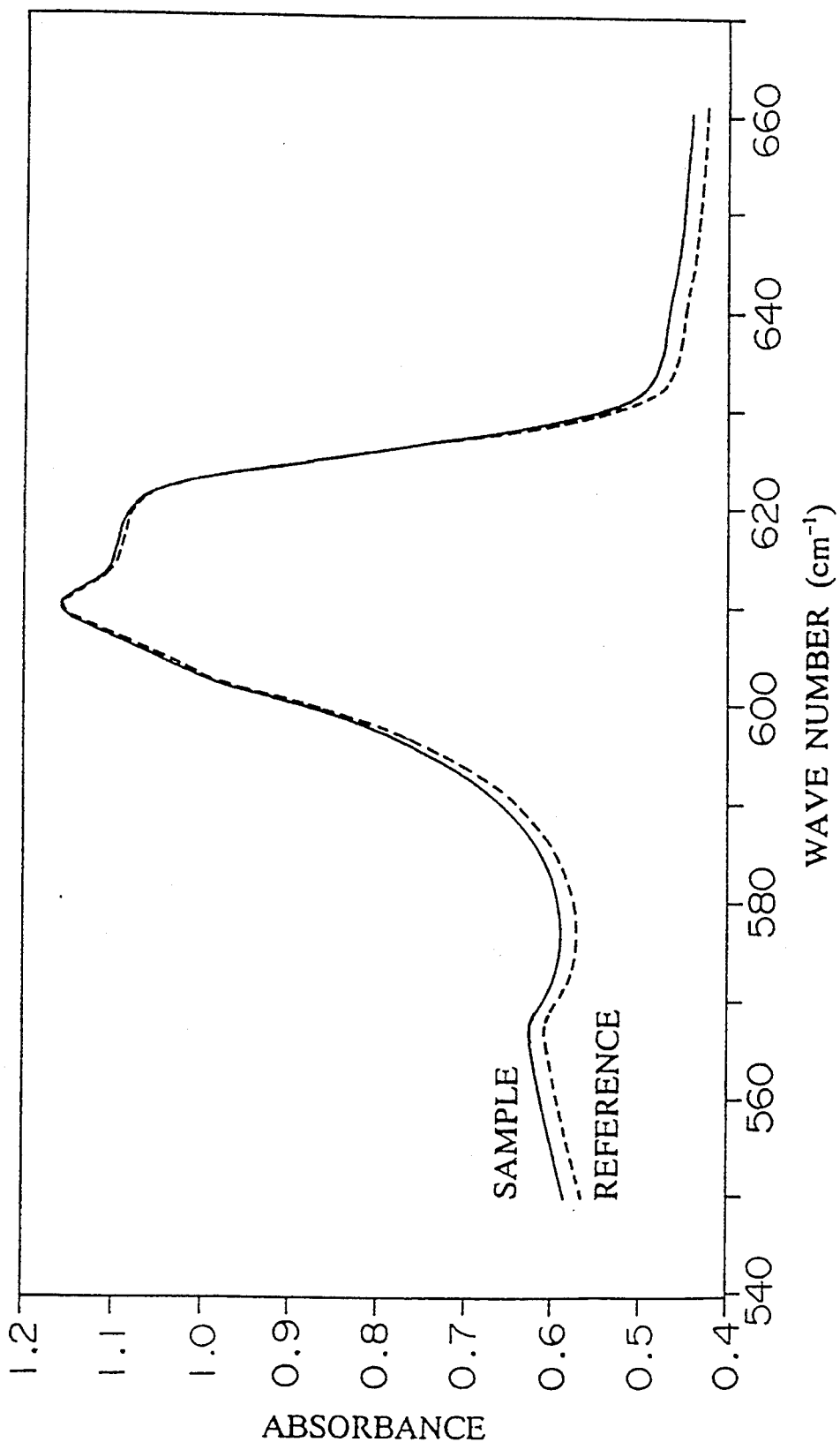
FIG. 7 is a graph of the infrared absorbance spectra of the sample and the reference.

As seen in FIG. 6, the absorption peak of the localized vibration of the substitutional carbon appears at 605 cm$^{-1}$, so that the lower range of wave number is Selected to be 550–595 cm$^{-1}$ and the higher range of wave number is selected to be 615–660 cm$^{-1}$. For example, $\kappa l1 = 550$ cm$^{-1}$ and $\kappa h2 = 660$ cm$^{-1}$ in the equations (4), (5), (6) and (7). The sample was a p-type CZ-method produced silicon single crystal of a resistivity of 10 $\Omega$cm and a carbon concentration of about 0.05 ppma. The reference was a carbon-free p-type CZ-method produced silicon single crystal of a resistivity of 20 $\Omega$cm. The apparatus determined the infrared absorbance spectra of the sample and the reference. FIG. 7 shows the infrared absorbance spectra of the sample and the reference.

Figure 8:
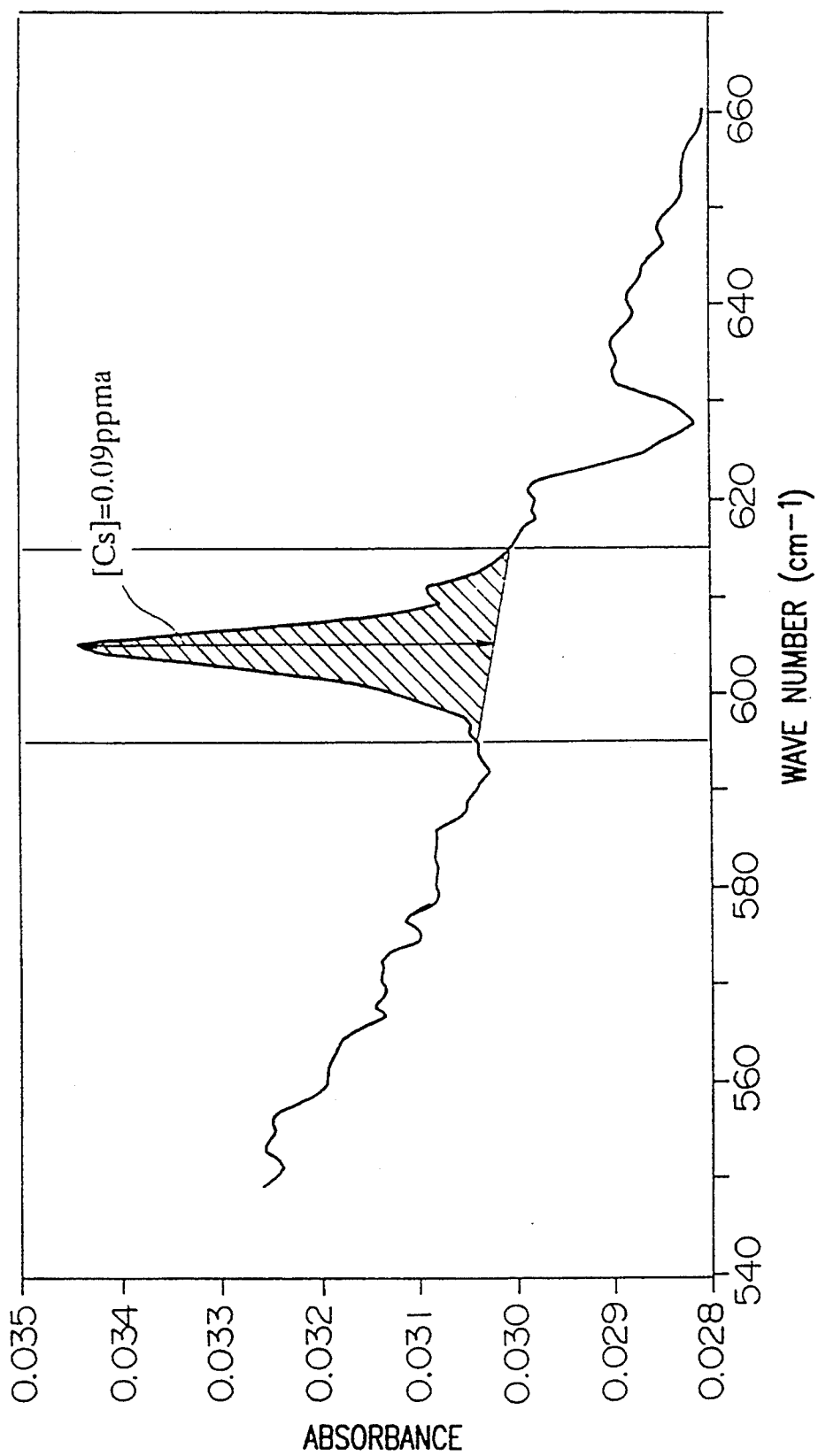
FIG. 8 is a graph indicative of the computed subtraction spectrum and the determination of the carbon concentration.
Figure 9:
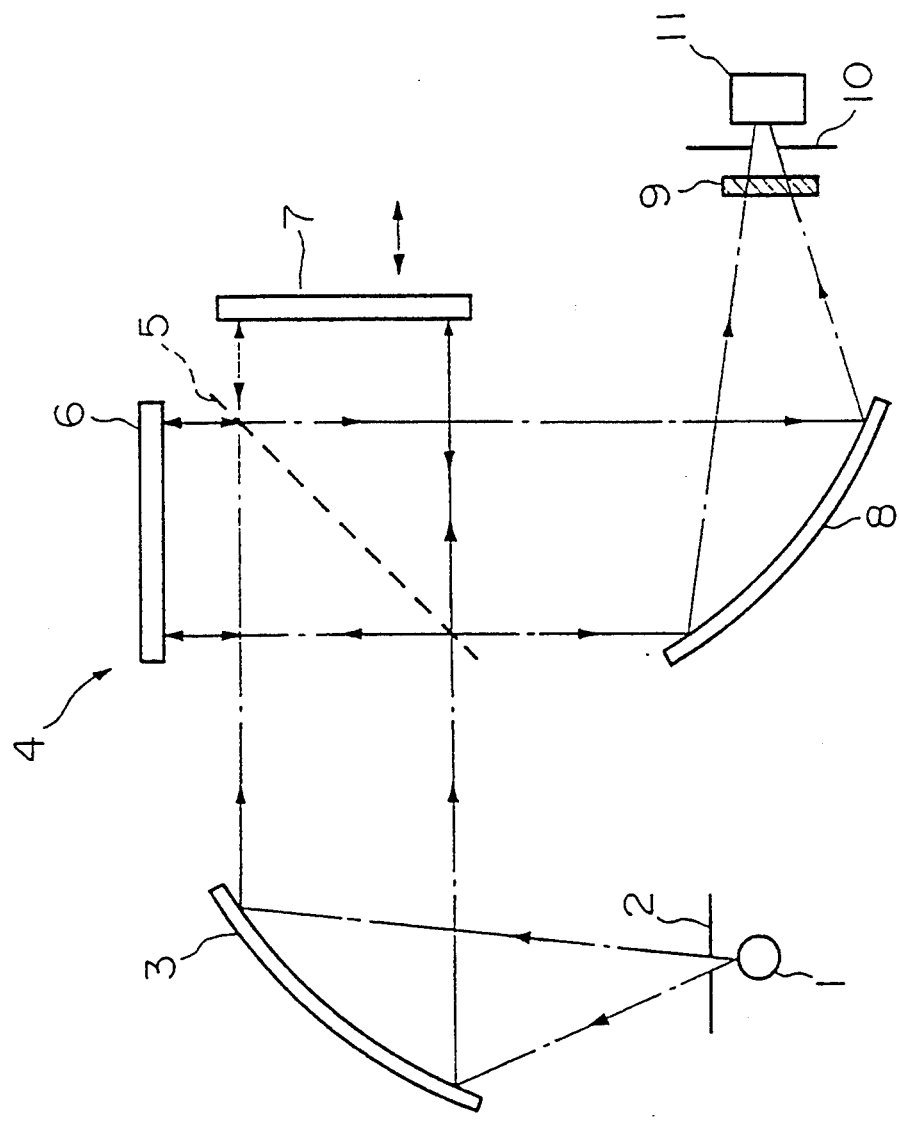
FIG. 9 is a schematic diagram of an FT-IR optical system.
Figure 10:
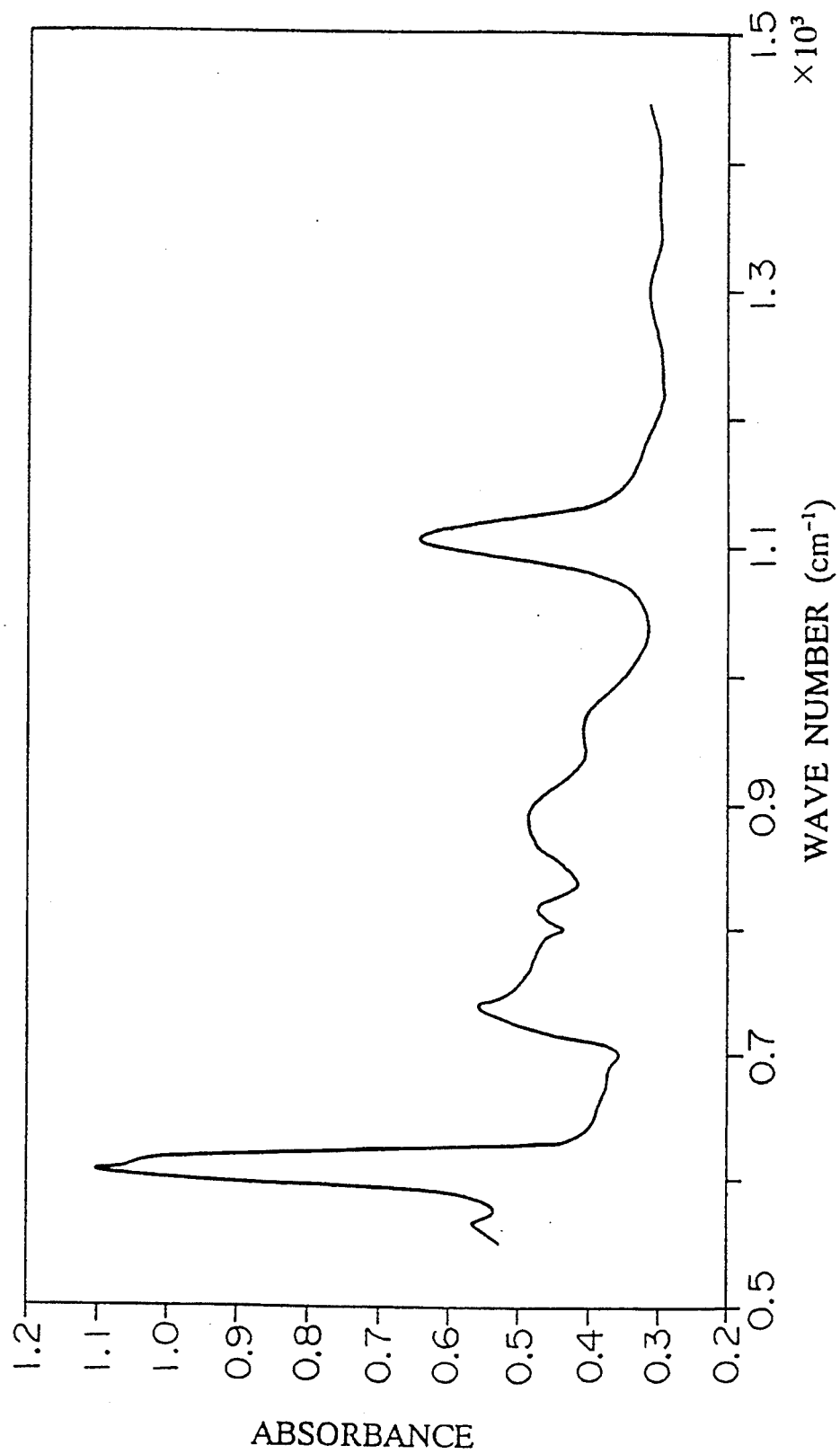
FIG. 10 is a graph of the infrared absorbance spectrum of the CZ-method produced silicon single crystal.
Figure 11:
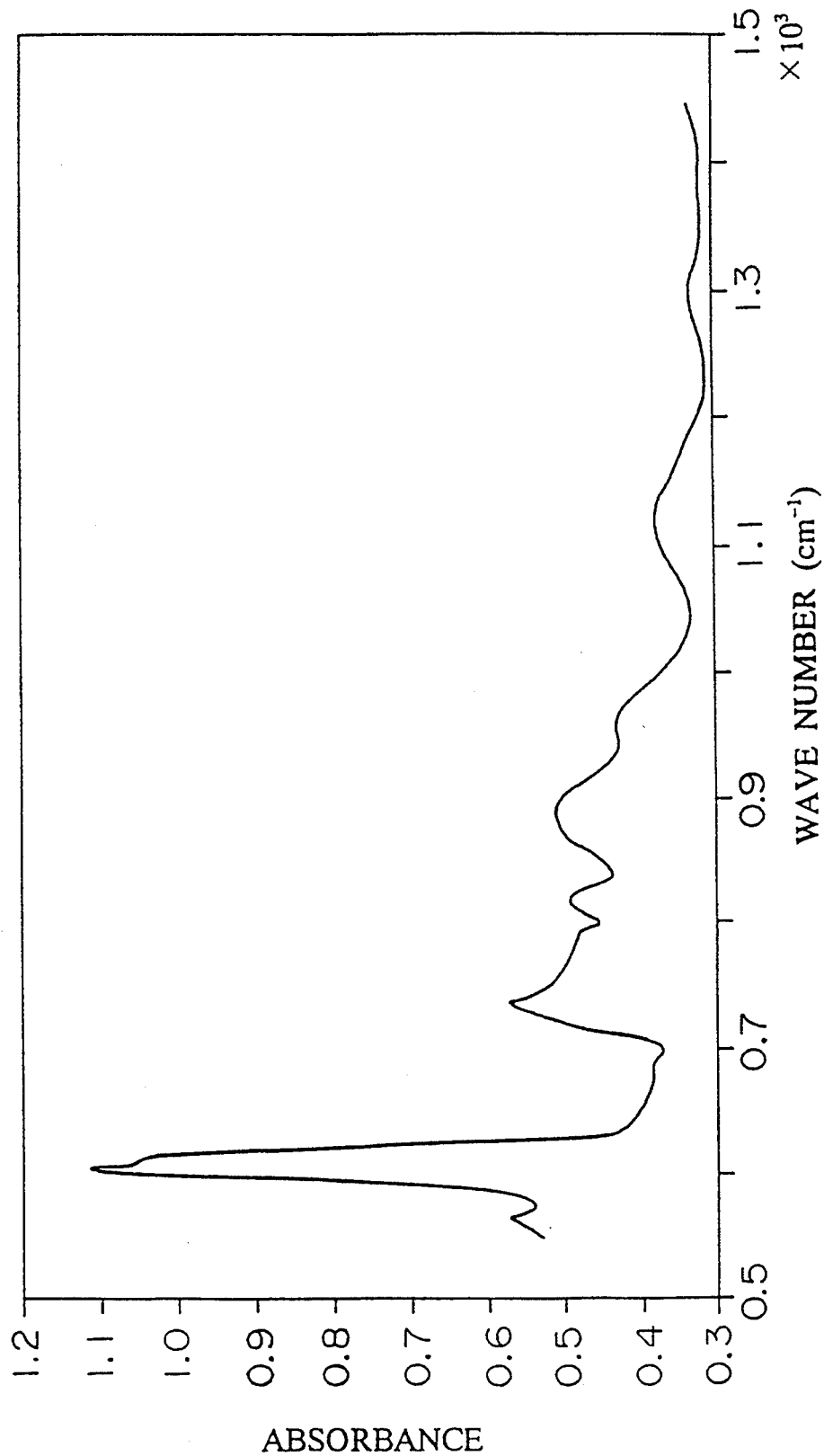
FIG. 11 is a graph of the infrared absorbance spectrum of the FZ-method produced silicon single crystal.
Figure 12:
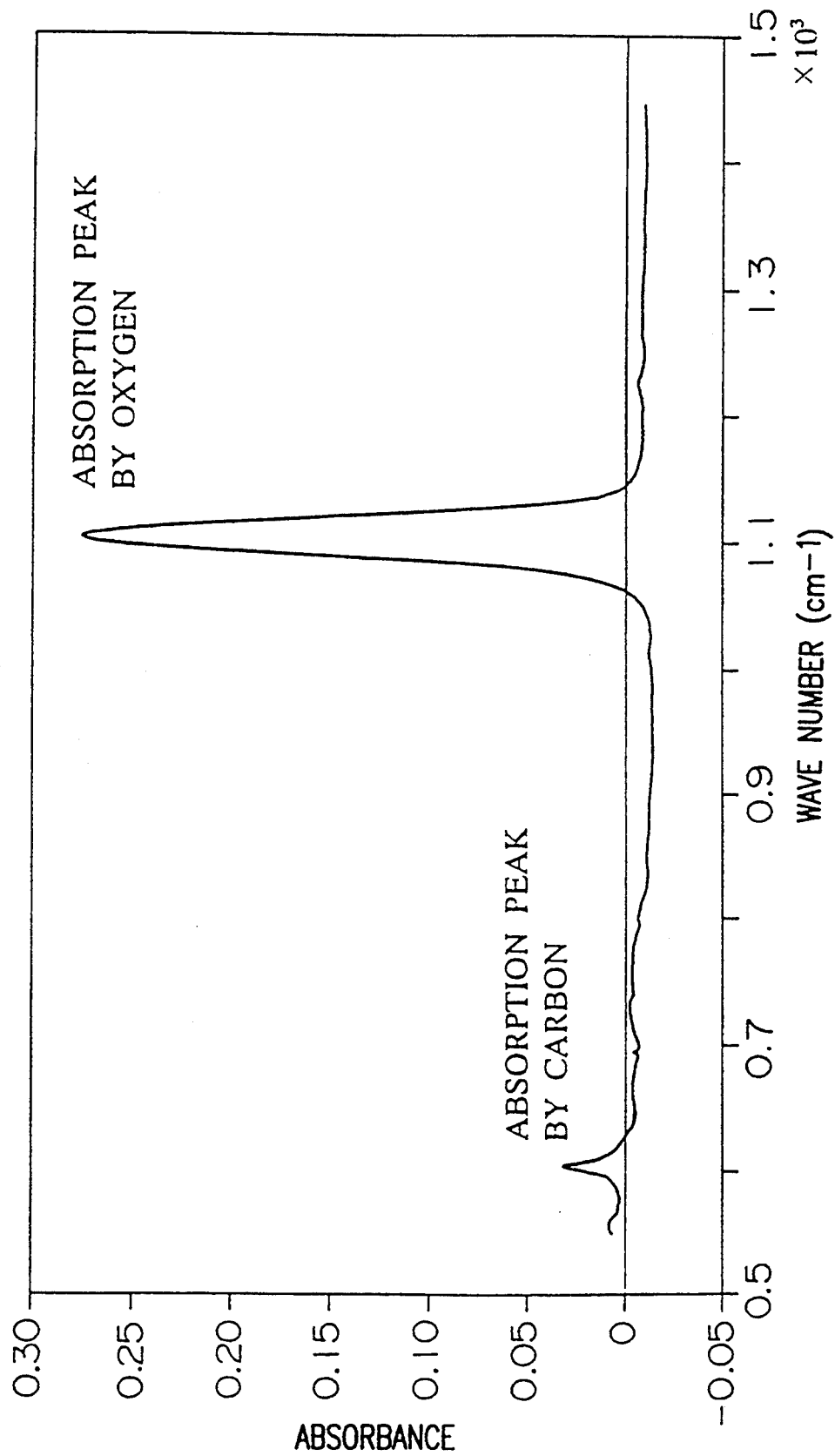
FIG. 12 is a graph of the subtraction spectrum between the CZ-method and FZ-method produced silicon single crystals computed by the prior-art method.
Figure 13:
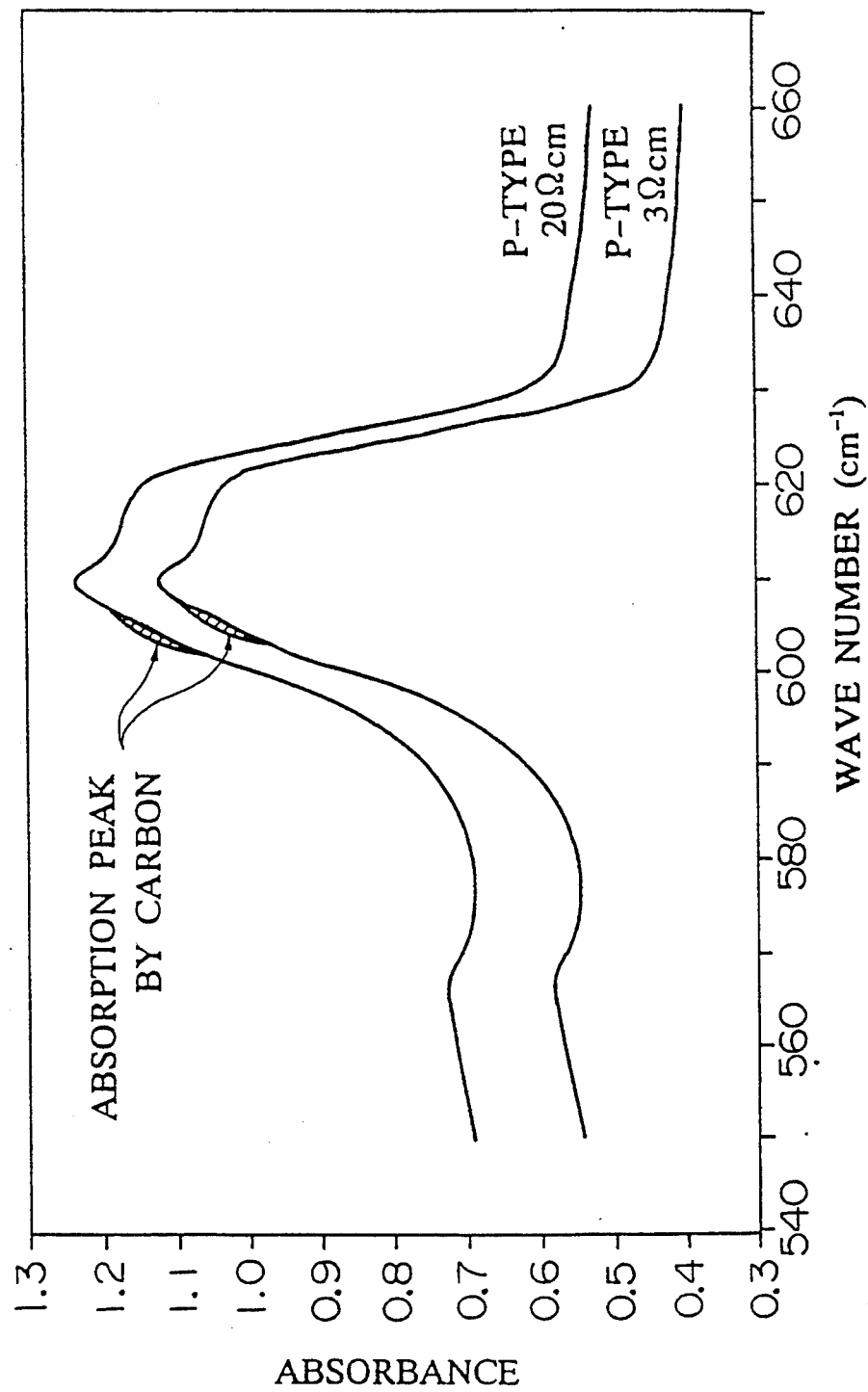
FIG. 13 is a graph of the infrared absorbance spectra, computed by the prior-art method, of CZ-method produced silicon single crystals of different resistivities.

The apparatus then computed the subtraction factor f by the equation (5) to provide 0.9764 and the subtraction spectrum from this value. FIG. 8 shows the subtraction spectrum provided by this computation. As seen in FIG. 8, the apparatus determined the carbon concentration [Cs] by ASTM designation: F123-81 to be 0.09 ppma using a base line of 595–615 cm$^{-1}$.

The present invention is not restricted to the determination of the carbon concentration of the P-type CZ-method produced silicon single crystal but is applicable to the determination of the carbon concentration in an N-type CZ-method produced silicon single crystal. In the latter case, the apparatus and the method employ a reference of a CZ-method produced silicon single crystal of substantially the same degree of free carrier absorption as a sample.

The present invention is also applicable to the determination of the carbon concentration in a FZ-method produced silicon single crystal. In this case, the apparatus and the method employ a reference of a substantially carbon-free FZ-methodical silicon single crystal.

The present invention is not rigidly restricted to the embodiments described above. It is to be understood that a person skilled in the art can easily change and modify the present invention without departing from the scope of the invention defined in the appended claims.

What is claimed is:

1. A method of determining the substitutional carbon concentration in a silicon single crystal by Fourier transform infrared spectroscopy (FT-IR), comprising the steps of:
   measuring by FT-IR the infrared absorbance spectrum of a sample of a silicon single crystal, a carbon concentration of which is to be determined;
   measuring by FT-IR the infrared absorbance spectrum of a reference of a substantially carbon-free silicon single crystal with substantially the same degree of free carrier absorption as the sample, the reference being produced by the same process as the sample;
   computing a subtraction factor from the infrared absorbance spectra of the sample and the reference;
   computing a subtraction spectrum between the infrared absorbance spectra of the sample and the reference using the computed subtraction factor; and
   determining the substitutional carbon concentration in the sample from a distance of the absorption peak of the subtraction spectrum of the localized vibration of the substitutional carbon in the sample from a base line of the subtraction spectrum.

2. The method as recited in claim 1, wherein said subtraction factor computing step comprises the step of computing the subtraction factor by a least square approximation so that a relational expression between wave number and infrared absorbance is approximate to a linear equation within first and second ranges of wave number which are lower and higher than that of the absorption peak of the subtraction spectrum of the localized vibration of the substitutional carbon, respectively.

3. The method as recited in claim 2, wherein the linear equation is the following equation (4):

$$S = \int_{\kappa=\kappa l1}^{\kappa=\kappa h1} [(As(\kappa) - f \times Ar(\kappa)) - (b\kappa + a)]^2 d\kappa + \int_{\kappa=\kappa l2}^{\kappa=\kappa h2} [(As(\kappa) - f \times Ar(\kappa)) - (b\kappa + a)]^2 d\kappa. \quad (4)$$

4. The method as recited in claim 2, wherein the linear equation is the following equation (5):

$$S = \int_{\kappa=\kappa l1}^{\kappa=\kappa h1} [(As(\kappa) - f \times Ar(\kappa)) - (b\kappa + a)]^2 + \int_{\kappa=\kappa l2}^{\kappa=\kappa h2} [(As(\kappa) - f \times Ar(\kappa)) - (b\kappa + a)]^2. \quad (5)$$

5. The method as recited in claim 1, wherein said subtraction factor computing step comprises the step of computing the subtraction factor by a least square approximation so that a relational expression between wave number and infrared absorbance is approximate to a quadratic equation within first and second ranges of wave number which are lower and higher than that of the absorption peak of the subtraction spectrum of the localized vibration of the substitutional carbon, respectively.

6. The method as recited in claim 5, wherein the quadratic equation is the following equation (6):

$$S = \int_{\kappa=\kappa l1}^{\kappa=\kappa h1} [(As(\kappa) - f \times Ar(\kappa)) - (c\kappa + b\kappa + a)]^2 d\kappa + \int_{\kappa=\kappa l2}^{\kappa=\kappa h2} [(As(\kappa) - f \times Ar(\kappa)) - (c\kappa + b\kappa + a)]^2 d\kappa. \quad (6)$$

7. The method as recited in claim 5, wherein the quadratic equation is the following equation (7):

$$S = \int_{\kappa=\kappa l1}^{\kappa=\kappa h1} [(As(\kappa) - f \times Ar(\kappa)) - (c\kappa^2 + b\kappa + a)]^2 d\kappa + \int_{\kappa=\kappa l2}^{\kappa=\kappa h2} [(As(\kappa) - f \times Ar(\kappa)) - (c\kappa^2 + b\kappa + a)]^2 d\kappa. \quad (7)$$

8. An apparatus for determining the substitutional carbon concentration in a silicon single crystal by Fourier transform infrared spectroscopy (FT-IR), comprising:
   means for measuring by FT-IR the infrared absorbance spectrum of a sample of a silicon single crystal, a substitutional carbon concentration of which is to be determined;
   means for storing data of the infrared absorbance spectra, measured by FT-IR, of multiple references of substantially carbon-free silicon single crystals of different degrees of free carrier absorption;

means for selecting data of the infrared absorbance spectrum of a reference of substantially the same degree of free carrier absorption as the sample from the data of the infrared absorbance spectra of the references in said storage means;

means for computing a subtraction factor from the infrared absorbance spectra of the sample and the selected reference;

means for computing a subtraction spectrum between the infrared absorbance spectra of the sample and the selected reference using the computed subtraction factor; and means for determining the substitutional carbon concentration in the sample from a distance of the absorption peak of the subtraction spectrum of the localized vibration of the substitutional carbon in the sample from a base line of the subtraction spectrum.

9. The apparatus as recited in claim 8, further comprising:

means for determining by FT-IR the infrared absorbance spectra of the references.

10. An apparatus for determining the substitutional carbon concentration in a silicon single crystal by Fourier transform infrared spectroscopy (FT-IR), comprising:

means for measuring by FT-IR the infrared absorbance spectrum of a sample of a silicon single crystal, a substitutional carbon concentration of which is to be determined;

means for storing data of the infrared absorbance spectra, measured by FT-IR, of multiple references of substantially carbon-free silicon single crystals of different degrees of free carrier absorption;

means for selecting data of the infrared absorbance spectrum of a reference of substantially the same degree of free carrier absorption as the sample from the data of the infrared absorbance spectra of the references in said storage means;

means for computing a subtraction factor from the infrared absorbance spectra of the sample and the selected reference by a least square approximation so that a relational expression between wave number and infrared absorbance is approximate to an equation within first and second ranges of wave number which are lower and higher than that of the absorption peak of the subtraction spectrum of the localized vibration of the substitutional carbon, respectively;

means for computing a subtraction spectrum between the infrared absorbance spectra of the sample and the selected reference using the computed subtraction factor; and means for determining the substitutional carbon concentration in the sample from a distance of the absorption peak of the subtraction spectrum of the localized vibration of the substitutional carbon in the sample from a base line of the subtraction spectrum.

11. The apparatus as recited in claim 10, further comprising:

means for determining by FT-IR the infrared absorbance spectra of the references.

12. A method of determining the substitutional carbon concentration in a Czochralski(CZ) method produced silicon single crystal by Fourier transform infrared spectroscopy (FT-IR), comprising the steps of:

measuring by FT-IR the infrared absorbance spectrum of a sample of the CZ-method produced silicon single crystal, the substitutional carbon concentration of which is to be determined;

measuring by FT-IR the infrared absorbance spectrum of a reference of a substantially carbon-free CZ-method produced silicon single crystal of substantially the same degree of free carrier absorption as the sample;

computing a subtraction factor from the infrared absorbance spectra of the sample and the reference;

computing a subtraction spectrum between the infrared absorbance spectra of the sample and the reference using the computed subtraction factor; and determining the substitutional carbon concentration in the sample from a distance of the absorption peak of the subtraction spectrum of the localized vibration of the substitutional carbon in the sample from a base line of the subtraction spectrum.

13. The method as recited in claim 12, wherein said subtraction factor computing step comprises the step of computing the subtraction factor by a least square approximation so that a relational expression between wave number and infrared absorbance is approximate to a linear equation within first and second ranges of wave number which are lower and higher than that of the absorption peak of the subtraction spectrum of the localized vibration of the substitutional carbon, respectively.

14. The method as recited in claim 13, wherein the linear equation is the following equation (4):

$$S = \int_{\kappa=\kappa l1}^{\kappa=\kappa h1} [(As(\kappa) - f \times Ar(\kappa)) - (b\kappa + a)]^2 d\kappa + \int_{\kappa=\kappa l2}^{\kappa=\kappa h2} [(As(\kappa) - f \times Ar(\kappa)) - (b\kappa + a)]^2 d\kappa. \quad (4)$$

15. The method as recited in claim 13, wherein the linear equation is the following equation (5):

$$S = \int_{\kappa=\kappa l1}^{\kappa=\kappa h1} [(As(\kappa) - f \times Ar(\kappa)) - (b\kappa + a)]^2 + \int_{\kappa=\kappa l2}^{\kappa=\kappa h2} [(As(\kappa) - f \times Ar(\kappa)) - (b\kappa + a)]^2. \quad (5)$$

16. The method as recited in claim 12, wherein said subtraction factor computing step comprises the step of computing the subtraction factor by a least square approximation so that a relational expression between wave number and infrared absorbance is approximate to a quadratic equation within first and second ranges of wave number which are lower and higher than that of the absorption peak of the subtraction spectrum of the localized vibration of the substitutional carbon, respectively.

17. The method as recited in claim 16, wherein the quadratic equation is the following equation (6):

$$S = \int_{\kappa=\kappa l1}^{\kappa=\kappa h1} [(As(\kappa) - f \times Ar(\kappa)) - (c\kappa^2 + b\kappa + a)]^2 d\kappa + \quad (6)$$

$$\int_{\kappa=\kappa l2}^{\kappa=\kappa h2} [(As(\kappa) - f \times Ar(\kappa)) - (c\kappa + b\kappa + a)]^2 d\kappa.$$

18. The method as recited in claim 16, wherein the quadratic equation is the following equation (7):

$$S = \int_{\kappa=\kappa l1}^{\kappa=\kappa h1} [(As(\kappa) - f \times Ar(\kappa)) - (c\kappa^2 + b\kappa + a)]^2 d\kappa + \qquad (7)$$

$$\int_{\kappa=\kappa l2}^{\kappa=\kappa h2} [(As(\kappa) - f \times Ar(\kappa)) - (c\kappa^2 + b\kappa + a)]^2 d\kappa.$$

19. An apparatus for determining the substitutional carbon concentration in a Czochralski (CZ) method produced silicon single crystal by Fourier transform infrared spectroscopy (FT-IR), comprising:
   means for storing data of the infrared absorbance spectra, measured by FT-IR, of multiple references of substantially carbon-free CZ-method produced silicon single crystals of different degrees of free carrier absorption;
   means for measuring by FT-IR the infrared absorbance spectrum of a sample of the CZ-method produced silicon single crystal, the substitutional carbon concentration of which is to be determined;
   means for selecting data of the infrared absorbance spectrum of a reference of substantially the same degree of free carrier absorption as the sample from the data in said storage means;
   means for computing a subtraction factor from the infrared absorbance spectra of the selected reference and the sample by a least square approximation so that a relational expression between wave number and infrared absorbance is approximate to an equation within first and second ranges of wave number which are lower and higher than that of the absorption peak of the subtraction spectrum of the localized vibration of the substitutional carbon, respectively;
   means for computing a subtraction spectrum between the infrared absorbance spectra of the sample and the selected reference using the computed subtraction factor; and
   means for determining the substitutional carbon concentration in the sample from the computed subtraction spectrum by a predetermined relation between carbon concentration and subtraction spectrum.

20. The apparatus as recited in claim 19, further comprising:
   means for determining by FT-IR the infrared absorbance spectra of the references.

21. The apparatus as recited in claim 19, wherein said equation is a linear equation.

22. The apparatus as recited in claim 21, wherein the linear equation is the following equation (4):

$$S = \int_{\kappa=\kappa l1}^{\kappa=\kappa h1} [(As(\kappa) - f \times Ar(\kappa)) - (b\kappa + a)]^2 d\kappa + \qquad (4)$$

$$\int_{\kappa=\kappa l2}^{\kappa=\kappa h2} [(As(\kappa) - f \times Ar(\kappa)) - (b\kappa + a)]^2 d\kappa.$$

23. The apparatus as recited in claim 21, wherein the linear equation is the following equation (5):

$$S = \int_{\kappa=\kappa l1}^{\kappa=\kappa h1} [(As(\kappa) - f \times Ar(\kappa)) - (b\kappa + a)]^2 + \qquad (5)$$

$$\int_{\kappa=\kappa l2}^{\kappa=\kappa h2} [(As(\kappa) - f \times Ar(\kappa)) - (b\kappa + a)]^2.$$

24. The apparatus as recited in claim 19, wherein said equation is a quadratic equation.

25. The apparatus as recited in claim 24, wherein the quadratic equation is the following equation (6):

$$S = \int_{\kappa=\kappa l1}^{\kappa=\kappa h1} [(As(\kappa) - f \times Ar(\kappa)) - (c\kappa + b\kappa + a)]^2 d\kappa + \qquad (6)$$

$$\int_{\kappa=\kappa l2}^{\kappa=\kappa h2} [(As(\kappa) - f \times Ar(\kappa)) - (c\kappa + b\kappa + a)]^2 d\kappa.$$

26. The apparatus as recited in claim 24, wherein the quadratic equation is the following equation (7):

$$S = \int_{\kappa=\kappa l1}^{\kappa=\kappa h1} [(As(\kappa) - f \times Ar(\kappa)) - (c\kappa^2 + b\kappa + a)]^2 d\kappa + \qquad (7)$$

$$\int_{\kappa=\kappa l2}^{\kappa=\kappa h2} [(As(\kappa) - f \times Ar(\kappa)) - (c\kappa^2 + b\kappa + a)]^2 d\kappa.$$

* * * * *